US008162149B1

(12) United States Patent  
Perroud et al.

(10) Patent No.: US 8,162,149 B1
(45) Date of Patent: Apr. 24, 2012

(54) PARTICLE SORTER COMPRISING A FLUID DISPLACER IN A CLOSED-LOOP FLUID CIRCUIT

(75) Inventors: Thomas D. Perroud, San Jose, CA (US); Kamlesh D. Patel, Dublin, CA (US); Ronald F. Renzi, Tracy, CA (US)

(73) Assignee: Sandia Corporation, Albuquerque, NM (US)

( * ) Notice: Subject to any disclaimer, the term of this patent is extended or adjusted under 35 U.S.C. 154(b) by 507 days.

(21) Appl. No.: 12/424,758

(22) Filed: Apr. 16, 2009

Related U.S. Application Data (60) Provisional application No. 61/146,100, filed on Jan. 21, 2009.

(51) Int. Cl.
*B07C 5/38* (2006.01)
(52) U.S. Cl. .................................. 209/631; 209/155
(58) Field of Classification Search ............... 209/631, 209/638, 906, 932
See application file for complete search history.

(56) References Cited

U.S. PATENT DOCUMENTS

| | | | |
|---|---|---|---|
| 5,101,978 A * | 4/1992 | Marcus | 209/3.1 |
| 6,432,630 B1 | 8/2002 | Blankenstein | |
| 6,744,038 B2 | 6/2004 | Wang et al. | |
| 6,778,724 B2 | 8/2004 | Wang et al. | |
| 6,784,420 B2 | 8/2004 | Wang et al. | |
| 6,790,330 B2 | 9/2004 | Gascoyne et al. | |
| 6,808,075 B2 | 10/2004 | Bohm et al. | |
| 6,815,664 B2 | 11/2004 | Wang et al. | |
| 6,833,542 B2 | 12/2004 | Wang et al. | |
| 6,838,056 B2 | 1/2005 | Foster | |
| 6,846,668 B1 | 1/2005 | Garman et al. | |
| 6,976,590 B2 * | 12/2005 | Deshpande et al. | 209/631 |
| 7,018,819 B2 | 3/2006 | Orwar et al. | |
| 7,068,874 B2 | 6/2006 | Wang et al. | |
| 7,069,943 B2 | 7/2006 | Gilbert et al. | |
| 7,081,192 B1 | 7/2006 | Wang et al. | |
| 7,104,405 B2 | 9/2006 | Bohm et al. | |
| 7,105,355 B2 | 9/2006 | Kurabayashi et al. | |
| 7,118,676 B2 | 10/2006 | Mueth et al. | |
| 7,138,269 B2 | 11/2006 | Blankenstein | |
| 7,153,648 B2 | 12/2006 | Jing et al. | |
| 7,157,274 B2 | 1/2007 | Bohm | |
| 7,214,298 B2 | 5/2007 | Spence et al. | |
| 7,241,988 B2 | 7/2007 | Gruber et al. | |
| 7,264,972 B2 | 9/2007 | Foster | |
| 7,270,986 B2 | 9/2007 | Mutz et al. | |
| 7,285,412 B2 | 10/2007 | Casagrande et al. | |
| 7,294,249 B2 | 11/2007 | Gawad et al. | |
| 7,294,503 B2 | 11/2007 | Quake et al. | |
| 7,312,085 B2 | 12/2007 | Chou | |
| 7,381,565 B2 | 6/2008 | Kurabayashi et al. | |
| 7,389,879 B2 | 6/2008 | Tyvoll | |
| 7,392,908 B2 | 7/2008 | Frazier | |

(Continued)

OTHER PUBLICATIONS

Keunho Ann; Charles Kerbage; Tom P. Hunt; R. M. Westervelt; Darren H. Link; D. A. Weitz; "Dielectrophoretic manipulation of drops for high-speed microfluidic sorting devices", Applied Physics Letters, 2006, 88, pp. 024104-1 to 024104-3.

Robert W. Applegate, Jr; Jeff Squier: Tor Vestad; John Oakey; David W. M. Marr: Philippe Bado; Mark A. Dugan; Ali A. Said; "Microfluidic sorting system based on optical waveguide integration and diode laser bar trapping", Lab on a Chip, 2006, 6, pp. 422-426.

(Continued)

*Primary Examiner* — Joseph C Rodriguez
*Assistant Examiner* — Kalyanavenkateshware Kumar
(74) *Attorney, Agent, or Firm* — Smith, Gambrell & Russell, LLP (57) ABSTRACT

Disclosed herein are methods and devices utilizing a fluid displacer in a closed-loop fluid circuit.

21 Claims, 5 Drawing Sheets

U.S. PATENT DOCUMENTS

| | | | |
|---|---|---|---|
| 7,402,131 | B2 | 7/2008 | Mueth et al. |
| 7,405,395 | B2 | 7/2008 | Ellson et al. |
| 2002/0005354 | A1 | 1/2002 | Spence et al. |
| 2002/0058332 | A1 | 5/2002 | Quake et al. |
| 2002/0121443 | A1 | 9/2002 | O'Connell |
| 2002/0123112 | A1 | 9/2002 | Wang et al. |
| 2002/0132316 | A1 | 9/2002 | Wang et al. |
| 2002/0181837 | A1 | 12/2002 | Wang et al. |
| 2003/0007894 | A1 | 1/2003 | Wang et al. |
| 2003/0044832 | A1 | 3/2003 | Blankenstein |
| 2003/0175980 | A1 | 9/2003 | Hayenga et al. |
| 2003/0178310 | A1 | 9/2003 | Gawad et al. |
| 2003/0234210 | A1 | 12/2003 | Deshpande et al. |
| 2004/0229349 | A1 | 11/2004 | Daridon |
| 2005/0063872 | A1 | 3/2005 | Foster |
| 2005/0106739 | A1* | 5/2005 | Cabuz et al. ............ 436/63 |
| 2005/0109410 | A1 | 5/2005 | Gilbert et al. |
| 2005/0164158 | A1 | 7/2005 | Wang et al. |
| 2005/0173313 | A1 | 8/2005 | Tyvoll et al. |
| 2005/0175981 | A1 | 8/2005 | Voldman et al. |
| 2005/0178700 | A1 | 8/2005 | Tyvoll et al. |
| 2005/0183995 | A1 | 8/2005 | Deshpande et al. |
| 2005/0207940 | A1 | 9/2005 | Butler et al. |
| 2006/0060767 | A1 | 3/2006 | Wang et al. |
| 2006/0062698 | A1 | 3/2006 | Foster et al. |
| 2006/0134599 | A1 | 6/2006 | Toner et al. |
| 2006/0177815 | A1 | 8/2006 | Soh et al. |
| 2006/0177940 | A1 | 8/2006 | Furst |
| 2006/0223185 | A1 | 10/2006 | Fedorov et al. |
| 2006/0266679 | A1 | 11/2006 | Bohm et al. |
| 2007/0029257 | A1 | 2/2007 | Mueth et al. |
| 2007/0059680 | A1 | 3/2007 | Kapur et al. |
| 2007/0065808 | A1 | 3/2007 | Bohm et al. |
| 2007/0131622 | A1 | 6/2007 | Oakey et al. |
| 2007/0172903 | A1 | 7/2007 | Toner et al. |
| 2007/0196820 | A1 | 8/2007 | Kapur et al. |
| 2007/0215528 | A1 | 9/2007 | Hayenga et al. |
| 2007/0231851 | A1 | 10/2007 | Toner et al. |
| 2007/0235640 | A1 | 10/2007 | Gruber et al. |
| 2007/0238169 | A1 | 10/2007 | Abilez et al. |
| 2007/0259424 | A1 | 11/2007 | Toner et al. |
| 2007/0264675 | A1 | 11/2007 | Toner et al. |
| 2008/0023399 | A1 | 1/2008 | Inglis et al. |
| 2008/0030865 | A1 | 2/2008 | Gilbert et al. |
| 2008/0087585 | A1 | 4/2008 | Tyvoll et al. |
| 2008/0093306 | A1 | 4/2008 | Oakey et al. |
| 2008/0124721 | A1 | 5/2008 | Fuchs et al. |
| 2008/0176211 | A1 | 7/2008 | Spence et al. |
| 2008/0180666 | A1 | 7/2008 | Gilbert et al. |

OTHER PUBLICATIONS

N. Reginald Beer; Benjamin J. Hindson; Elizabeth K. Wheeler: Sara B. Hall; Klint A. Rose; I. M. Kennedy; Bill W. Colston; On-Chip, Real-Time, Single-Copy Polymerase Chain Reaction in Picoliter Droplets, Analytical Chemistry, 2007, 79, pp. 8471-8475.
Sung Hwan Cho: Jessica Godin: Chun Hao Chen; Frank S. Tsai; Yu-Hwa Lo: "Microfluidic Photonic Integrated Circuits", Proceedings of SPIE, vol. 7135, pp. 71350M-1 to 71350M-10.
Petra S. Dittrich; Petra Schwille; "An Integrated Microfluidic System for Reaction, High-Sensitivity Detection, and Sorting of Fluorescent Cells and Particles". Analytical Chemistry, 2003, 75, pp. 5767-5774.
Anne Y, Fu; Hou-Pu Chou; Charles Spence; Frances H. Arnold; Stephen R. Quake; "An Integrated Microfabricated Cell Sorter", Analytical Chemistry, 2002, 74, 2451-2457.
Anne Y. Fu; Charles Pence; Axel Scherer; Frances H. Arnold; Stephen R, Quake; "A microfabricated fluorescence-activated cell sorter", Nature Biotechnology, 1999, 17, pp. 1109-1111.
Mingyan He; J. Scott Edgar: Gavin D. M. Jeffries; Robert M. Lorenz; J. Patrick Shelby; Daniel T. Chiu, "Selective Encapsulation of Single Cells and Subcellular Organelles into Picoliter- and Femtoliter-Volume Droplets", Analytical Chemistry, 2005, 77, pp. 1539-1544.
Chen-Ta Ho; Ruei-Zeng Lin; Hwan-You Chang; Cheng-Hsien Liu; "Micromachined electrochemical T-switches for cell sorting applications" Lab on a Chip, 2005, 5, pp. 1248-1258.
Xiaoyuan Hu; Paul H. Bessette; Jiangrong Qian; Carl D. Meinhart; Patrick S. Daugherty; Hyongsok T. Soh: "Marker-specific sorting of rare cells using dielectrophoresis", PNAS, 2005, 102(44), pp. 15757-15761.
A. Huebner: M. Srisa-Art; D. Holt; C. Abell; F. Hollfelder; A. J. Demello; J. B. Edel; "Quantitative detection of protein expression in single cells using droplet microfluidics", Chemical Communications, 2007, pp. 1218-1220.
Yeong-Cheol Kim; Praneet Adusumilli; Lincoln J. Lauhon; David N. Seidman; Roger L. Alvis; Rob M. Ulfig; Jesse D. Olson; "Three-dimensional atomic-scale mapping of Pd in Ni1-xPDxSi/Si(100) thin films", Applied Physics Letters, 2007, 91, pp. 113106-1 to 113106-3.
Unyoung Kim; Chih-Wen Shu; Karen Y. Dane; Patrick S. Daugherty; Jean Y. J. Wang; H. T. Soh; "Selection of mammalian cells based on their cell-cycle phase using dielectrophoresis", PNAS, 2007, 104(52), pp. 20708-20712.
J. R. Kovac; J. Voldman; "Intuitive, Image-Based Cell Sorting Using Optofluidic Cell Sorting", Analytical Chemistry, 2007, 79, pp. 9321-9330.
Jan Kruger; Kirat Singh; Alan O'Neill; Carl Jackson; Alan Morrison; Peter O'Brien; "Development of a microfluidic device for fluorescence activated cell sorting", Journal of Micromechanics and Microengineering, 2002, 12, pp. 486-494.
Blanca H. Lapizco-Encinas; Blake A. Simmons; Eric B. Cummings; Yolanda Fintschenko; "Dielectrophoretic Concentration and Separation of Live and Dead Bacteria in an Array of Insulators", Analytical Chemistry, 2004, 76(6), pp. 1571-1579.
Hyejin Moon; Aaron R. Wheeler; Robin L. Garrell; Joseph A. Loo; Chang-Jin "CJ" Kim; An integrated digital microfluidic chip for multiplexed proteomic sample preparation and analysis by MALDI-MS, Lab on a Chip, 2006, 6, pp. 1213-1219.
Thomas D. Perroud; Julia N. Kaiser; Jay C. Sy; Todd W. Lane; Catherine S. Branda; Anup K. Singh; Kamlesh D. Patel; Microfluidic-Based Cell Sorting of *Francisella tularensis* Infected Macrophages Using Optical Forces, Analytical Chemistry, 2008, 80, pp. 6365-6372.
Yoshitaka Shirasaki; Jyunichi Tanaka; Hiroshi Makazu; Koichiro Tashiro; Shuichi Shoji; Shoichiro Tsukita; Takashi Funatsu; "On-Chip Cell Sorting System Using Laser-Induced Heating of a Thermoreversible Gelation Polymer to Control Flow", Analytical Chemistry, 2006, 78(3), pp. 695-701.
Helen Song; Rustem F. Ismagilov; Millisecond Kinetics on a Microfluidic Chip Using Nanoliters of Reagents, Journal of American Chemical Society, 2003, 125, pp. 14613-14619.
Daniel J. Throckmorton; Timothy J. Shepodd; Anup K. Singh; "Electrochromatography in Microchips: Reversed-Phase Separation of Peptides and Amino Acids Using Photopatterned Rigid Polymer Monoliths", Analytical Chemistry, 2002, 74(4), 784-789.
Mark M. Wang; Eugene Tu; Daniel E. Raymond; Joon Mo Yang; Haichuan Zhang; Norbert Hagen; Bob Dees; Elinore M. Mercer; Anita H. Forster, Ilona Kariv, Philippe J. Marchand; William F. Butler; "Microfluidic sorting of mammalian cells by optical force switching", Nature Biotechnology, 2005, 23(1), pp. 83-87.
A. Wolff; J. R. Perch-Nielsen; U. D. Larsen; P. Friis; G. Goranovic, C. R. Poulsen; J. P. Kutter; P. Telleman; "Integrating advanced functionality in a microfabricated high-throughput fluorescent-activated cell sorter", Lab on a Chip, 2003, 3, pp. 22-27.
Eugene Tu; Haichuan Zhang; Mark M. Wang; Daniel E. Raymond; Joon Mo Yang; Norbert Hagen; Bob Dees; Elinore M. Mercer; Anita H. Forster; Soheil Attari; Chris Richardson; Ilona Kariv; Mirianas Chachisvillis; Manami Hara; Philippe J. Marchand; William F. Butler; "Microfluidic cell analysis and sorting using photonic forces", Proceedings of SPIE, Bellingham, WA, 2004, vol. 5514, pp. 774-785.
Chunxiong Luo; Hao Li; Chunyang Xiong; Xiaoling Peng; Qingli Kou; Yong Chen; Hang Ji; Qi Ouyang; "The combination of optical tweezers and microwell array for cells physical manipulation and localization in microfluidic device", Biomed Microdevices; 2007, 9, pp. 573-578.
Thomas D. Perroud; Robert J. Meagher; Michael P. Kanouff; Ronald F. Renzi; Meiye Wu; Anup K. Singh; Kamlesh D. Patel; "Isotropically etched radial micropore for cell concentration, immobilization, and picodroplet generation", Lab Chip, 2009, 9, pp. 507-515.
Sung Hwan Cho*, et al., Microfluidic Photonic Integrated Circuits, Proc. of SPIE, vol. 7135, pp. 71350M-1 to 71350M-10, *scho@logroup.ucsd.edu; phone 1 858 822-2777; fax 1 858 534-0556; Keywords: Microfluidics, Photonics, Sensor, On-Chip optics, Flow Cytometry, FACS.

\* cited by examiner

PARTICLE SORTER COMPRISING A FLUID DISPLACER IN A CLOSED-LOOP FLUID CIRCUIT

CROSS-REFERENCE TO RELATED APPLICATIONS

This application claims the benefit of U.S. Provisional Patent Application Ser. No. 61/146,100, filed 21 Jan. 2009, which is herein incorporated by reference in its entirety.

ACKNOWLEDGEMENT OF GOVERNMENT SUPPORT

The U.S. Government has a paid-up license in this invention and the right in limited circumstances to require the patent owner to license others on reasonable terms as provided for by the terms of Contract No. DE-AC04-94AL85000 between the Department of Energy and Lockheed Martin Corporation for the management and operation of Sandia National Laboratories.

BACKGROUND OF THE INVENTION

1. Field of the Invention

The present invention generally relates to methods and devices for sorting particles in a fluid using a fluid displacer in a closed-loop.

2. Description of the Related Art

In the fields of biotechnology, and especially cytology and drug screening, there is a need for high throughput sorting of particles. Many prior art methods and devices for particle sorting are based on the detect-decide-deflect principle in which moving particles suspended in a liquid flowing through a channel network having at least a branch point downstream are first analyzed for a given characteristic and then deflected according to the characteristic in the direction of a predetermined branch or area of the channel network.

Numerous sorting strategies for micro fluidic-based particle sorting are known in the art. Some prior art sorting techniques include electrokinetic flow switching (see e.g. Fu et al. (1999) Nature Biotech. 17:1109-1111 and Dittrich et al. (2003) Anal. Chem. 75:5767-5774); hydrodynamic flow switching using on-chip (see e.g. Fu et al. (2002) Anal. Chem. 74:2451.2457) and off-chip valves (see e.g. Kruger et al. (2002) Micromech. & Microengineer. 12:486-494 and Wolff et al. (2003) Lab on a Chip 3:22-27); MEMS-based micro-T switches (see e.g. Ho et al. (2005) Lab on a Chip 5:1248-1258); and a thermoreversible gelation polymer (see e.g. Shirasaki et al. (2006) Anal. Chem. 78:695-701). Dielectrophoretic approaches for cell sorting include segregation of tagged cells (see e.g. Hu et al. (2005) PNAS USA 102:15757-15761); untagged cells (see e.g. Lapizco-Encinas et al. (2004) Anal. Chem. 76:1571-1579, and Kim et al. (2007) PNAS USA 104:20708-20712) and droplets (and Ahn et al. (2006) Applied Physics Letts 88:24104-24101. Optical sorting has been achieved by binning particles into one (see e.g. Tu et al. Optical Trapping and Optical Micromanipulation; Dholakia, K., Spalding, G. C., Eds., 2004; Vol. 5514, pp 774-785, Wang et al. (2005) Nature Biotech. 23:83-87, and Perroud et al. (2008) Anal. Chem. 80:6365-6372) or more channels (see e.g. Applegate et al. (2006) Lab on a Chip 6:422-426) and manipulating individual cells within an array of microwells (see e.g. Luo et al. (2007) Biomedical Microdevices 9:573-578 and Kovac et al. (2007) Anal. Chem. 79:9321-9330); and Cho et al. (2008) Proc. of SPIE 7135:71350 M1-10).

Some prior art methods employ a piezoelectric element to shift the fluid surrounding the particle of interest towards a desired area, thereby sorting or separating the particle of interest from other particles in the fluid flow that has not been shifted. See, for example, U.S. Pat. Nos. 7,157,274; 7,312,085; 7,389,879; and 7,392,908.

Unfortunately, these prior art piezoelectric-based sorters suffer from creating a transient pressure gradient during the deflection affecting the steady-state flow stream upstream and downstream of the deflection region. Since the detection region is upstream of the deflection region, the velocity and trajectory of subsequent particles is affected by the deflection of the particle of interest. This change in velocity or trajectory creates a jitter effect in the detection region affecting the accuracy of the detection.

Therefore, a need exists for methods and devices which sort individual particles with high efficiency and throughput in a cost-effective way without disturbing the flow pattern upstream, downstream, or both of the deflection region.

SUMMARY OF THE INVENTION

Prior art methods and devices for the sorting of particles rely on the physical, chemical, and biological properties of the particles for efficient sorting, e.g. optical sorting relies on the refractive index or optical polarizability of the particles, dielectrophoretic sorting relies on the dielectrophoretic properties of the particles, and magnetic sorting relies on the magnetism of the particles. According to the present invention, the sorting of particles is achieved by the displacement of a fluid packet, which is independent of the physical, chemical, and biological properties of the particles. Therefore, the present invention is more versatile, especially for highly heterogeneous samples, than prior art methods and devices.

The present invention provides methods and devices which sort individual particles with high efficiency and throughput in a cost-effective way by displacing a plug of fluid (fluid packet) where the particle of interest is without disturbing the flow pattern upstream, downstream, or both of the deflection region (area in which the plug of fluid is displaced). According to the present invention, displacement of the plug is able to occur without disturbing the flow pattern by use of a fluid displacer in a closed-loop fluid circuit. When the fluid displacer is activated, its deflection generates equal volumes of fluidic displacement in a simultaneous "push-and-pull" manner.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIGS. 1A-1C schematically show a fluid displacer (e.g. a piezo-actuated element) positioned within a closed-loop fluid circuit deflecting a particle of interest by displacing a fluid packet).

As shown in FIG. 2B, an off-chip piezo-actuated element is positioned as a drumhead between two hollow mounts. Spring-loaded POGO pins, located inside the mounts, form an electrical connection with the piezo-actuated element. The fluidic circuit comprises tubing connecting the outlet of each hollow mount to the manifold, which interfaces with the microfluidic chip.

FIGS. 3A-3D show the sorting of 5-μm particles and 15-μm particles based on their different forward scattering signatures according to the present invention.

FIGS. 4A and 4B schematically show two closed-loop fluid circuits with five different sorting combinations.

DETAILED DESCRIPTION OF THE INVENTION

The present invention relates to methods and devices which employ a fluid displacer, such as a piezo-actuated element, to sort particles in a fluidic channel.

As used herein, "channel" refers to a structure wherein a fluid may flow. A channel may be a capillary, a conduit, a strip of hydrophilic pattern on an otherwise hydrophobic surface wherein aqueous fluids are confined, and the like. As used herein, "microfluidic" refers to a system or device having one or more fluidic channels, conduits or chambers that are generally fabricated at the millimeter to nanometer scale. Thus, the "microfluidic channels" or alternatively referred to herein as "microchannels" of the present invention generally have cross-sectional dimensions ranging from about 10 nm to about 1 mm.

As used herein, a "particle" may be natural or synthetic chemicals or biological entities. Chemicals and biological entities (biomolecules) include industrial polymers, powders, latexes, emulsions, colloids, environmental pollutants, pesticides, insecticides, drugs such as cocaine and antibiotics, magnetic particles, high-magnetic-permeability particles, metal ions, metal ion complexes, inorganic ions, inorganic ion complexes, organometallic compounds, metals including aluminum, arsenic, cadmium, chromium, selenium, cobalt, copper, lead, silver, nickel, and mercury, and the like, amino acids, peptides, proteins, glycoproteins, nucleotides, nucleic acid molecules, carbohydrates, lipids, lectins, cells, viruses, viral particles, bacteria, organelles, spores, protozoa, yeasts, molds, fungi, pollens, diatoms, toxins, biotoxins, hormones, steroids, immunoglobulins, antibodies, supermolecular assemblies, ligands, catalytic particles, zeolites, and the like, biological and chemical warfare agents, agents used in explosives, and the like.

As used herein, a "fluid" refers to a continuous substance that tends to flow and to conform to the outline of a container such as a liquid or a gas. Fluids include saliva, mucus, blood, plasma, urine, bile, breast milk, semen, water, liquid beverages, cooking oils, cleaning solvents, ionic fluids, air, and the like. Fluids can also exist in a thermodynamic state near the critical point, as in supercritical fluids. If one desires to test a solid sample for a given particle according to the present invention, the solid sample may be made into a fluid sample using methods known in the art. For example, a solid sample may be dissolved in an aqueous solution, ground up or liquefied, dispersed in a liquid medium, melted, digested, and the like. Alternatively, the surface of the solid sample may be tested by washing the surface with a solution such as water or a buffer and then testing the solution for the presence of the given particle.

A fluid sample may include any particle mixture of interest. Particles, as used herein, may include any set of discrete, small objects. For example, the particles may be less than about 100 micrometers in diameter, and may be biological, synthetic, naturally occurring, organic, inorganic, or a combination thereof. Exemplary particles may include cells. The cells may be alive or dead, fixed or unfixed, processed or unprocessed, cultured or non-cultured, and/or the like. Exemplary cells may include eukaryotic cells and/or bacteria. Other exemplary particles may include viruses, organelles, vesicles, synthetic polymers, beads, coded beads carrying biomolecules, magnetic particles, and/or the like.

Exemplary sources for sample fluids may include a sample obtained from a subject (such as blood, a tissue biopsy, mucus, saliva, urine, sperm, tears, sweat, etc.), an environmental sample (such as a sample from water, air, soil, etc.), and/or a research sample, and the like.

The sample fluid may be preprocessed before sorting. For example, the sample fluid may be treated to make a subset of the particles optically distinguishable. In some embodiments, the sample fluid may be treated with a label, such as a dye, an optically active nanoparticle, or the like, to selectively label a subset of the particles. The label may be any optically detectable material. The label may bind directly to the particles or bind through a coupled (covalently or non-covalently) specific binding member, such as an antibody, a lectin, a molecular imprinted polymer, a nucleic acid, a receptor, a ligand, and the like. Alternatively, or in addition, the input mixture may be cells that have been engineered, such as by transfection, to express an optically detectable material, such as green fluorescent protein.

According to the methods and devices of present invention, a particle of interest in a fluid sample is deflected towards a given area by using a fluid displacer to displace the fluid surrounding the particle. As used herein, a "fluid displacer" refers to an object, such as a piezo-actuated element, an electro-magnetically actuated plunger, a diaphragm, a disk gear-pump, an electrokinetic pump, and the like, capable of displacing a volume of liquid on one side while simultaneously displacing the same volume of liquid on the other side. The fluid displacer may be unidirectional, i.e. only capable of displacing fluid (on both sides) in one direction (e.g. to the right), or bidirectional, i.e. capable of displacing the fluid to the right or the left. As used herein, the fluid surrounding a particle of interest is referred to as a "fluid packet" or "plug of fluid".

According to the present invention, the fluid displacer (e.g. a piezo-actuated element) is positioned within a fluid circuit which transverses the primary flow of the fluid sample. As used herein, a "fluid circuit" refers to a conduit that links, in a closed-loop, both sides of a fluid displacer to the primary flow of the fluid sample. Activation of the fluid displacer causes a secondary flow which is the flow of the fluid in the fluid circuit in a direction transverse to the primary flow. When the fluid displacer is activated, the fluid packet, containing the particle and located at the intersection between the primary flow and the fluid circuit, is shifted by the secondary flow, thereby changing the position and movement of the particle towards the given area.

According to the present invention, the fluid displacer is considered to be in a "closed-loop" fluid circuit. For example, when the fluid displacer is a piezo-actuated element, the convex side of the piezo-actuated element pushes the fluid in the fluid circuit at the same time the concave side of the piezo-actuated element pulls the fluid in the fluid circuit. This "closed-loop" feature allows the complete conservation of fluid in the fluid circuit during deflection, regardless of the physical characteristics (directionality, amplitude, frequency, shape) of the displacement of the fluid packet. The complete conservation of fluid during the deflection does not induce flow perturbation upstream or downstream of the deflection region in the primary flow therefore not affecting the accuracy of the particle detection, which is located upstream of the deflection region in the primary flow. In addition, the simultaneous pushing and pulling by the fluid displacer results in a greater degree of deflection in a shorter amount of time. Prior art methods based on displacement of a fluid packet by a piezo-actuated element displace the fluid packet into the primary flow that contains the sample. Thus, according to prior art methods, the fluid packet is either compressed into the primary flow or partially displaced in the opposite direction of the primary flow or both, which decreases the extent and velocity of the displacement of the fluid packet. For these reasons, the deflection of the fluid packet using a fluid displacer in a "closed-loop" fluid circuit according to the present invention is significantly better than prior art methods.

In a closed-loop fluid circuit according to the present invention, the volume of the two conduits that link both sides of the fluid displacer to the primary channel of the fluid sample is preferably equal to suppress transient pressure gradients in the primary channel of the fluid sample during each particle deflection. When the fluid displacer is not integrated in the microfluidic chip, the volume of the two conduits of the fluid displacer is preferably minimized such that efficiency of the fluid displacer is maximized, preferably about 0.1 to 100 microliters, and more preferably about 1 to 10 microliters. When the fluid displacer is integrated in the microfluidic chip, the volume of the two conduits of the fluid displacer is preferably minimized such that efficiency of the fluid displacer is maximized, preferably about 1 to 1000 nanoliters, and more preferably about 10 to 100 nanoliters.

At the intersection between the primary flow and the closed-loop fluid circuit, the cross-section of the conduits of the closed-loop fluid circuit defines the width, length and depth of the fluid packet. For a given fluid packet volume, a small cross section will result in a long length fluid packet, but a large cross-section will result in a short length. The length roughly equates to the distance an entrained particle is deflected. The preferred method is to introduce and remove a fluid packet of volume equal to the dimensions of the primary channel at the intersection of the fluid circuit conduits. When the fluid displacer is not integrated in the microfluidic chip, the preferred intersection volume is 1 to 1000 mL, and more preferably 1 to 100 mL.

The fluid in the closed-loop fluid circuit is preferably compatible with the primary flow. In addition, the fluid is preferably of good properties to couple well with the physical displacement of the fluid displacer. Good properties include low compressibility, low viscosity, low thermal coefficient of expansion. Examples of fluids that demonstrate these good properties include all aqueous solutions and dissolved ionic solutions, low molecular weight polyethylene glycol solutions (1-5% weight/volume) ratio, and nonorganic solvents like methanol, ethanol, isopropanol and the like.

Figure 1A:
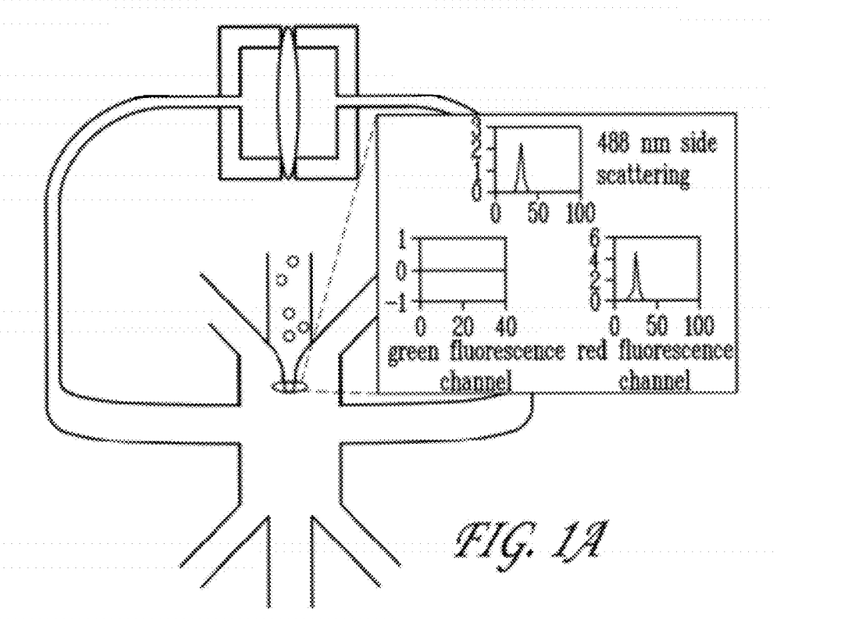
FIG. 1A shows a particle of interest in a fluid sample being detected in a fluidic channel using methods known in the art. The inset shows the signals on the forward scattering and red fluorescence detectors.
Figure 1B:
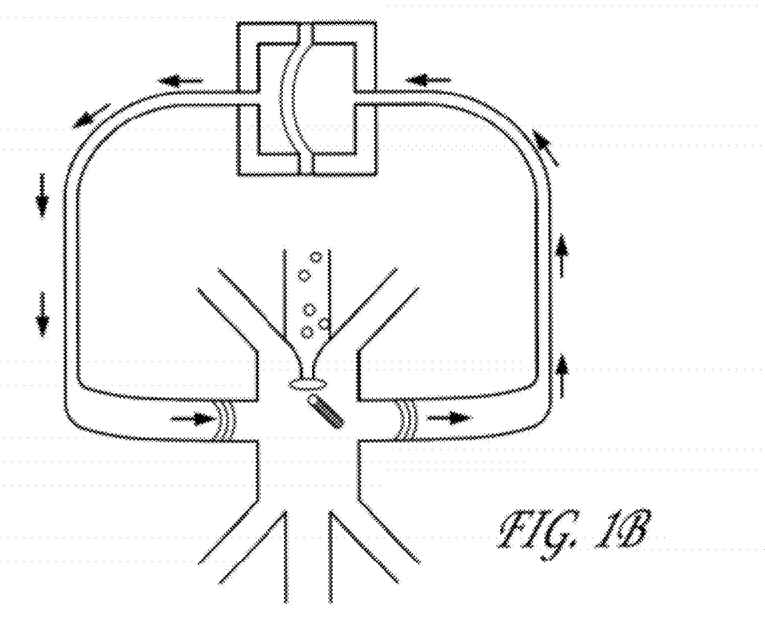
FIG. 1B shows activation of a piezo-actuated element in a fluid circuit which shifts the fluid packet and the particle therein.
Figure 1C:
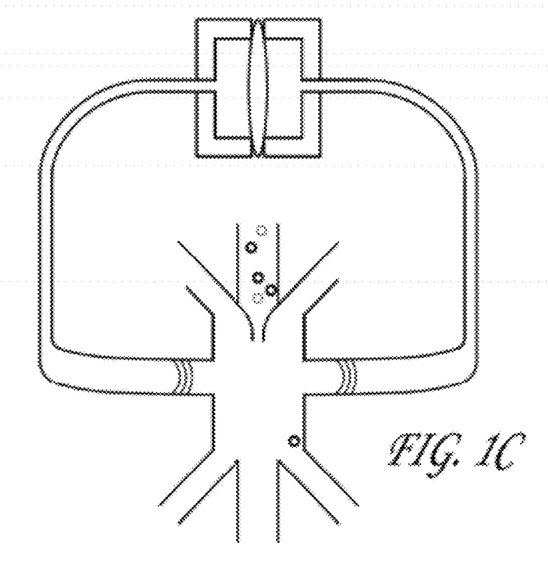
FIG. 1C shows the particle released in a different laminar flow stream moving towards a different area of the fluidic channel or a second fluidic channel or area.

FIG. 1A schematically shows a particle of interest in a fluid sample being detected in a fluidic channel using methods known in the art. FIG. 1B shows activation of a fluid displacer, e.g. a piezo-actuated element, in a fluid circuit which shifts the fluid packet and the particle therein. FIG. 1C shows the particle released in a different laminar flow stream moving towards a different area of the fluidic channel or a second fluidic channel or area.

In some embodiments, the particles in a fluid sample may be focused to flow in single file using methods known in the art, e.g. use of nozzles, hydrodynamical focusing, electrokinetic focusing, dielectrophoretic focusing, acousto-focusing, optical focusing, and the like, to improve the uniformity and accuracy of detection signals. When a particle passes through a detection area in a microchannel, the particle is detected using methods known in the art, e.g. laser induced fluorescence, Raman spectroscopy, laser scattering, and the like. If the particle is identified as being a particle of interest, then the particle of interest is deflected by a transverse fluid pulse into a different laminar flow stream by activating (bending) a fluid displacer, such as a piezo-actuated element (e.g. a piezoceramic disk), positioned in a fluidic circuit which is in fluidic communication with the primary flow of the fluid sample. The fluid displacer may be on- or off-chip.

The physical characteristics of the displacement of the fluid packet containing the particle of interest are determined by the physical characteristics of the fluid displacer and its activation. For example, the directionality of the displacement of the fluid packet is defined by the polarity of the amplified voltage signal applied to the piezo-actuated element. The extent of the displacement of the fluid packet is proportional to the amplitude of the amplified voltage signal applied to the piezo-actuated element. The velocity of the displacement of the fluid packet is defined by the frequency of the amplified voltage signal applied to the piezo-actuated element. The velocity of the displacement of the fluid packet can thus be adjusted to be equal or greater than the particle velocity. The maximum rate of successive displacement of the fluid packet is limited by the resonant frequency of the piezo-actuated element, which defines the maximum throughput of the particle sorter. By decreasing the cross-section of piezo-actuated element, higher resonant frequencies can be attained but at the expense of the extent of the displacement of the fluid packet. The type of displacement of the fluid packet depends on the shape (e.g. square shape, sinusoidal shape, triangle shape, positive/negative ramp shape, or any arbitrary shape) of the amplified voltage signal applied to the piezo-actuated element.

A device according to the present invention has the advantage of a small footprint, relative low cost, and high efficiency as compared to prior art sorters which employ deflection mechanisms based on optical forces, electrokinetic forces, dielectrophoretic forces, magnetic forces, gravitational forces or other mechanical forces. Specifically, the devices according to the present invention which have a small footprint may be employed as point-of-care devices and portable devices and used where space, transport and maintenance of larger devices is limited, such as in Biosafety Level 3 or 4 facilities and out in the field.

Figure 2A:
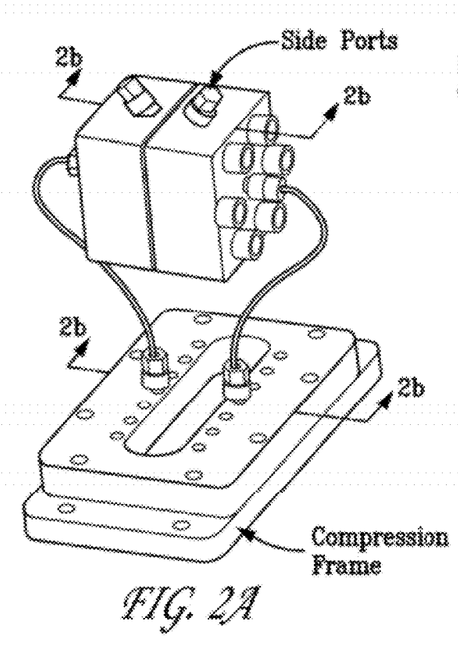
FIGS. 2A and 2B schematically show an example of a device according to the present invention.
Figure 2B:
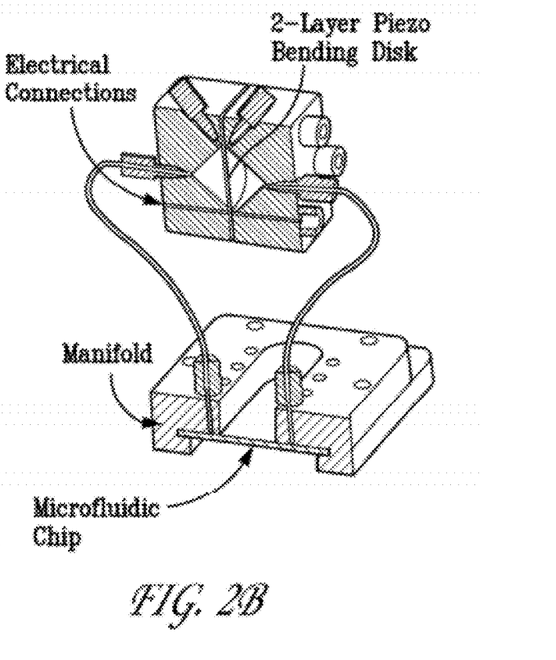

FIGS. 2A and 2B schematically show an example of a device according to the present invention. As shown in FIG. 2B, an off-chip piezo-actuated element is positioned as a drumhead between two hollow mounts. Spring-loaded POGO pins, located inside the mounts, form an electrical connection with the piezo-actuated element. Piezo-actuated elements such as a commercially available 2-layer piezo bending disk (T216-A4NO-273×, Piezo Systems Inc., Woburn, Mass.), stacked piezo-elements, extending piezo-elements, and the like, may be used in accordance with the present invention. The fluidic circuit comprises tubing connecting the outlet of each hollow mount to the manifold. The fluidic seal between each hollow mount and each side of the piezo-actuated element is obtained by using raised-ring protrusions that crush on the piezo-actuated element upon even compression of the two hollow mounts. This approach minimizes the amount of elastomeric material, which may be detrimental to the overall efficiency of the deflection by absorbing the displacement energy through compression. In some embodiments, the devices and methods of the present invention may employ side ports to purge air bubbles, which may be detrimental to the overall efficiency of the deflection by absorbing the displacement energy through compression.

In some embodiments, the fluid displacer can be integrated in the microfluidic chip. For example, a fluid displacer, such as a piezo-actuated element, can be sandwiched between two wafers of a microfluidic chip in which one side of the piezo-actuated element is fluidically connected to the primary flow of the sample via one wafer while the other side of the piezo-actuated element is fluidically connected to the primary flow of the sample via the second wafer.

In some embodiments, the fluid displacer, such as a piezo-actuated element, can be integrated in the interface manifold with reservoirs of the microfluidic chip. For example, the piezo-actuated element can be embedded in the interface manifold, where each side of the piezo-element is fluidically connected to a conduit of the manifold that is in fluidic communication with the microfluidic chip.

Figure 3A:
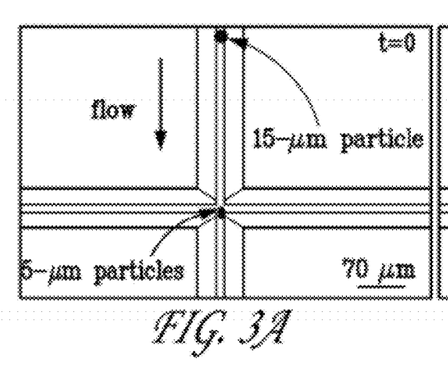
FIG. 3A shows a hydrodynamically focused 15-μm particle flowing at a velocity of 65 mm/s.
Figure 3B:
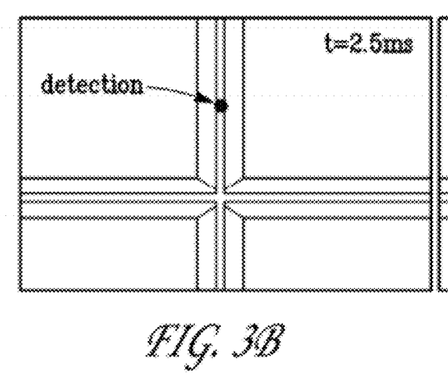
FIG. 3B shows the 15-μm particle detected by forward scattering.
Figure 3C:
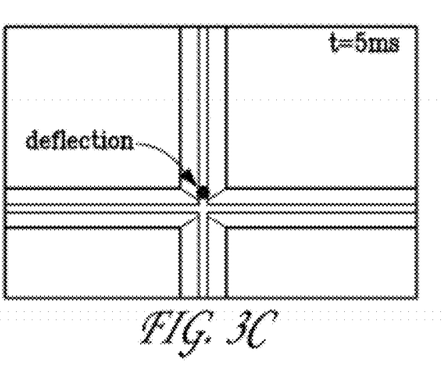
FIG. 3C shows activation of the piezo-actuated element by this forward scattering signal, which induces a rapid (less than about 1 ms) displacement (about 50 μm) of a fluid packet to the right.
Figure 3D:
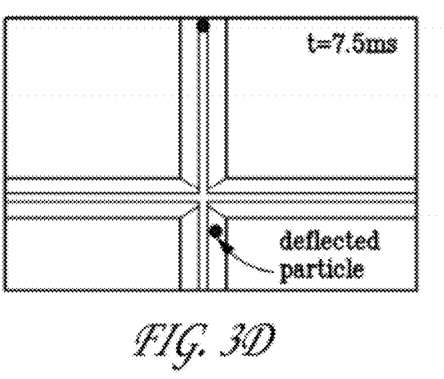
FIG. 3D shows the 15-μm particle positioned in a different laminar flow stream moving towards a different area for downstream binning.

FIGS. 3A-3D show the sorting of 5-μm particles (Microgenics, Fremont, Calif.) and 15-μm particles (Microgenics, Fremont, Calif.) based on their different forward scattering signatures according to the present invention. Specifically, 15-μm particles are selectively deflected by displacement of a fluid packet into a different laminar flow stream using a piezo-actuated element in a closed-loop fluid circuit. FIG. 3A shows a hydrodynamically focused 15-μm particle flowing at a velocity of 65 mm/s. FIG. 3B shows the 15-μm particle detected by forward scattering of 488 nm solid-state laser (Cyan; Newport, Irvine, Calif.). The forward scattering signal is detected through an optical fiber (JTFSH 600 μm core; Polymicro Technologies, Phoenix, Ariz.) and a bandpass filter with blocker (488NB2.6; Omega, Brattleboro, Vt.) connected to a photomultiplier (H5784-20; Hamamatsu, Bridgewater, N.J.). The photomultiplier voltage is processed by a custom-made digital counter to register each event and select the sorting decision signal. This signal initiates a precise time-delayed transistor-transistor-logic pulse (DG535; Stanford Research System, Palo Alto, Calif.), provided that the voltage peak exceeds a preset minimum threshold (3.5 V), which differentiates 15-μm particles from 5-μm particles. The time delay (1 ms) is calculated by dividing the distance between the detection region and the deflection region (70 μm) with the velocity of the particles (65 mm/s). This transistor-transistor-logic pulse is sent to a function generator (HP33120A; Agilent, Santa Clara, Calif.), which sends a 5-V squared-shape voltage pulse at a frequency of 1,000 Hz to the voltage amplifier (EPA-007-012, Piezo Systems, Inc, Woburn, Mass.). This squared-shape voltage pulse is further amplified to 200 V and applied to the piezo-actuated element through POGO pins. FIG. 3C shows activation of the piezo-actuated element (e.g. bending of a piezo-ceramic disk) which induces a rapid (less than about 1 ms) displacement (about 50 μm) of a fluid packet to the right. FIG. 3D shows the 15-μm particle positioned in a different laminar flow stream moving towards a different area for downstream binning. The overall throughput, which represents the average number of particles analyzed per unit of time, was 187 particles/s.

The device used for the experiment of FIGS. 3A-3D comprised a microfluidic chips, a Delrin manifold, PEEK tubing, and a piezoceramic element positioned as a drumhead between two hollow mounts.

The microfluidic chip was designed and fabricated as follows: The chrome/quartz photomask (F62CQ6120; Photo-Sciences, Torrance, Calif.) for the microfluidic chips was designed in L-Edit layout editor (Tanner Research, Inc. Monrovia, Calif.) using methods known in the art. The chips were fabricated using wet-etch and photolithographic methods known in the art. See Throckmorton et al. (2002) Anal. Chem. 74:784-789, which is herein incorporated by reference. Microchannels were isotropically etched in 0.70-mm-thick fused-silica base wafers. The final etch depth was measured across the wafer using a Tencor Alpha-Step profilometer (KLA-Tencor, Inc. Milpitas, Calif.) calibrated on a daily basis. Fluid access holes (500-μm diameter) were ultrasonically drilled into a cover wafer before being visually aligned and thermally bonded to the base wafer. The combined wafers were then diced with a wafer saw into individual 22.6×37.2 mm chips. Prior to each use, the channels were coated with a PBS buffered solution (pH 7.4) having 4% bovine serum albumin to prevent particle or cell adhesion to the walls.

The microfluidic chip packaging was performed as follows: A custom-made Delrin manifold with integrated 0.026 O.D. 0.022 I.D. Buna-N O-ring seals (Apple Rubber Products, Lancaster, N.Y.) provides the interface between the microfluidic chip and fluid reservoirs. Fluid was delivered to each port of the manifold through 1/32" O.D. 0.005" I.D. PEEK tubing (1576; Upchurch Scientific, Oak Harbor, Wash.) and swaged in place with 1/32" TubeTite fittings (Labsmith, Livermore, Calif.). Screw-cap microcentrifuge tubes (2.0 ml-89004-302; VWR, West Chester, Pa.) fitted with custom-machined caps served as fluid reservoirs. The caps have two ports to allow the delivery of $N_2$ gas to pressurize the headspace in the vial and push the fluid through a PEEK tube placed below the liquid level into the chip. All fluid reservoirs were pressurized by individual electronic pressure control units (VSO-EP; Parker, Cleveland, Ohio) to ensure precise control of pressure drops across the microfluidic chip. Flow rates were measured by Nano Flow sensors (N-565; UpChurch Scientific Oak Harbor, Wash.) calibrated against a syringe pump at room temperature prior to use.

The off-chip piezo-actuated element comprised a 2-layer piezo bending disk (T216-A4NO-273×, Piezo Systems Inc., Woburn, Mass.) positioned as a drumhead between two custom-made Kel-F polymeric conical hollow mounts. Spring-loaded POGO pins (C-S-R; Everett Charles Technologies, Pomona, Calif.), located inside the mounts, form an electrical connection with the piezo-actuated element. The fluidic circuit comprised tubing connecting the outlet of each Kel-F polymeric conical hollow mount to each port of the manifold through 1/32" O.D. 0.005" I.D. PEEK tubing (1576; Upchurch Scientific, Oak Harbor, Wash.) and swaged in place with 1/32" TubeTite fittings (Labsmith, Livermore, Calif.).

Figure 4A:
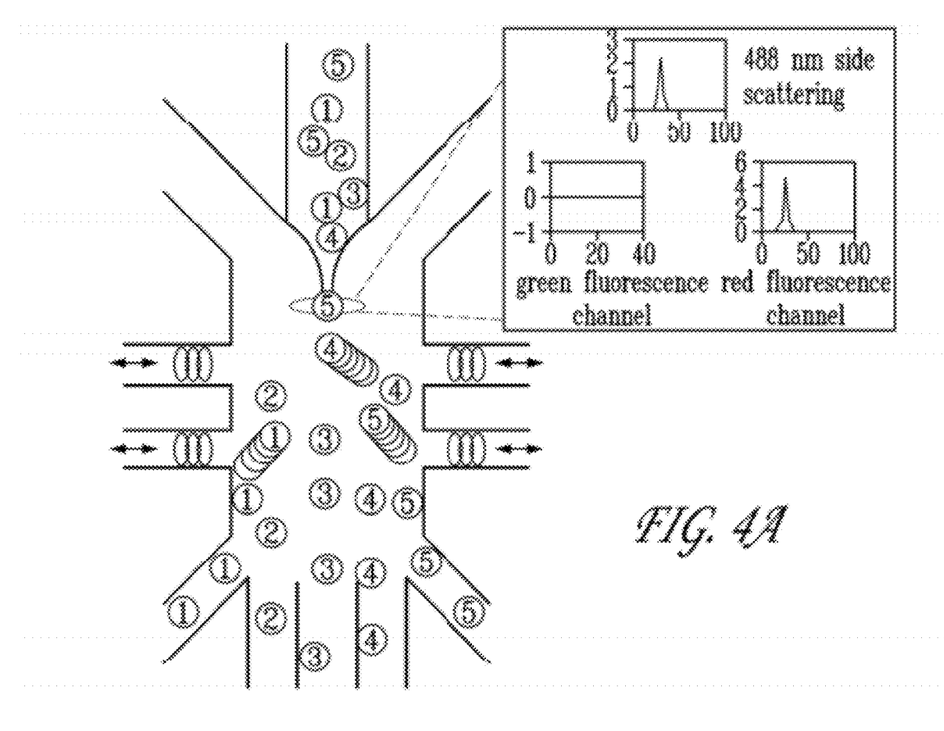
FIG. 4A shows two closed-loop fluid circuits successively arranged along the length of the primary microchannel sorting a mixture of particles numbered 1 to 5 into five different microchannels. The inset shows the signals on the forward scattering and red fluorescence detectors. As exemplified in FIG. 4B, the resulting 5 unique sorting combinations are left-left for particle number 1, left-neutral for particle number 2, neutral-neutral for particle number 3, right-neutral for particle number 4, and right-right for particle number 5.
Figure 4B:
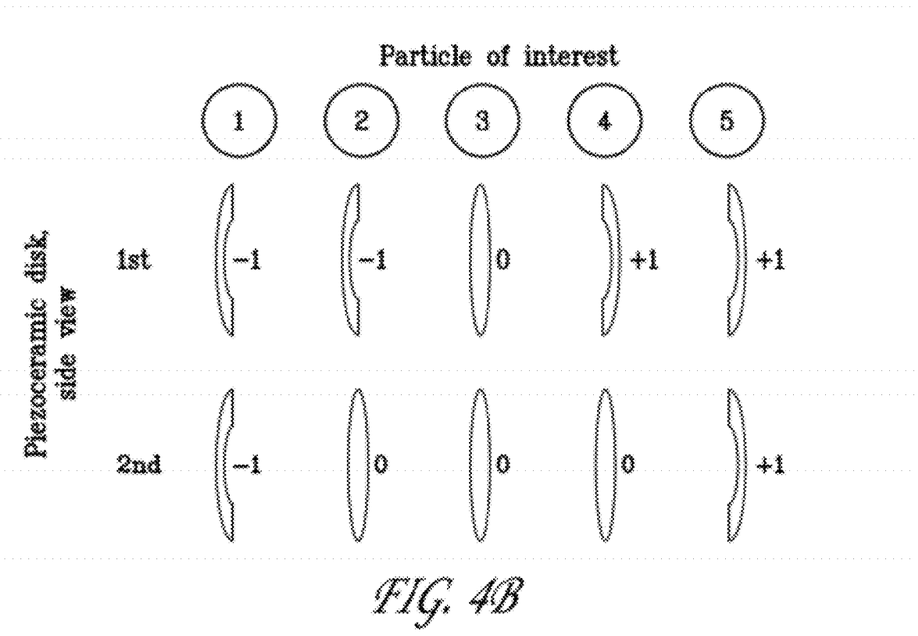

In some embodiments, the methods and devices of the present invention may comprise two or more closed-loop fluid circuits having fluid displacers, e.g. piezo-actuated elements. In these embodiments, the closed-loop fluid circuits are successively In re. Perroud et al. application Ser. No. 12/424,758 arranged along the length of a microchannel. The total number of unique sorting combinations is (2n+1), where n corresponds to the number of fluid displacers. FIGS. 4A and 4B schematically show two closed-loop fluid circuits with five different sorting combinations. FIG. 4A shows two closed-loop fluid circuits successively arranged along the length of the primary micro channel sorting a mixture of particles numbered 1 to 5 into five different microchannels. If the displacement of a fluid packet induced by the fluid displacer is considered as a quantum unit, this particle sorter represents a balanced ternary system where the digits have the values −1 (left), 0 (neutral), and +1 (right). As exemplified in FIG. 4B, the resulting 5 unique sorting combinations are left-left (−1; −1) for particle number 1, left-neutral (−1; 0) for particle number 2, neutral-neutral (0; 0) for particle number 3, right-neutral (0; +1) for particle number 4, and right-right (+1; +1) for particle number 5.

In some embodiments, the methods and devices of the present invention may comprise two or more orthogonal closed-loop fluid circuits perpendicular to the primary flow to allow both horizontal and vertical displacement of fluid packet. The total number of unique sorting combinations for this 3-dimensional sorter of particles is (6n−3), where n corresponds to the number of fluid displacers, e.g. piezo-actuated elements. For example, a sorter with two orthogonal closed-loop fluid circuits perpendicular to the primary flow gives 9 different sorting combinations. If the horizontal displacement of fluid packet induced by the first fluid displacer is defined as left, neutral, and right, and the vertical displacement of fluid packet induced by the second fluid displacer is defined as up, neutral, and down. the resulting 9 unique sorting combinations are: up-left, up-neutral, up-right, neutral-left, neutral-neutral, neutral-right, down-left, down-neutral, and down-right.

In some embodiments, the methods and devices of the present invention may comprise at least two closed-loop fluid circuits having fluid displacers, e.g. piezo-actuated elements, successively arranged along the length of a microchannel and at least two orthogonal closed-loop fluid circuits perpendicular to the primary flow, preferably about 2 to 10, more preferably about 2 to 5 closed-loop fluid circuits.

Figure 5:
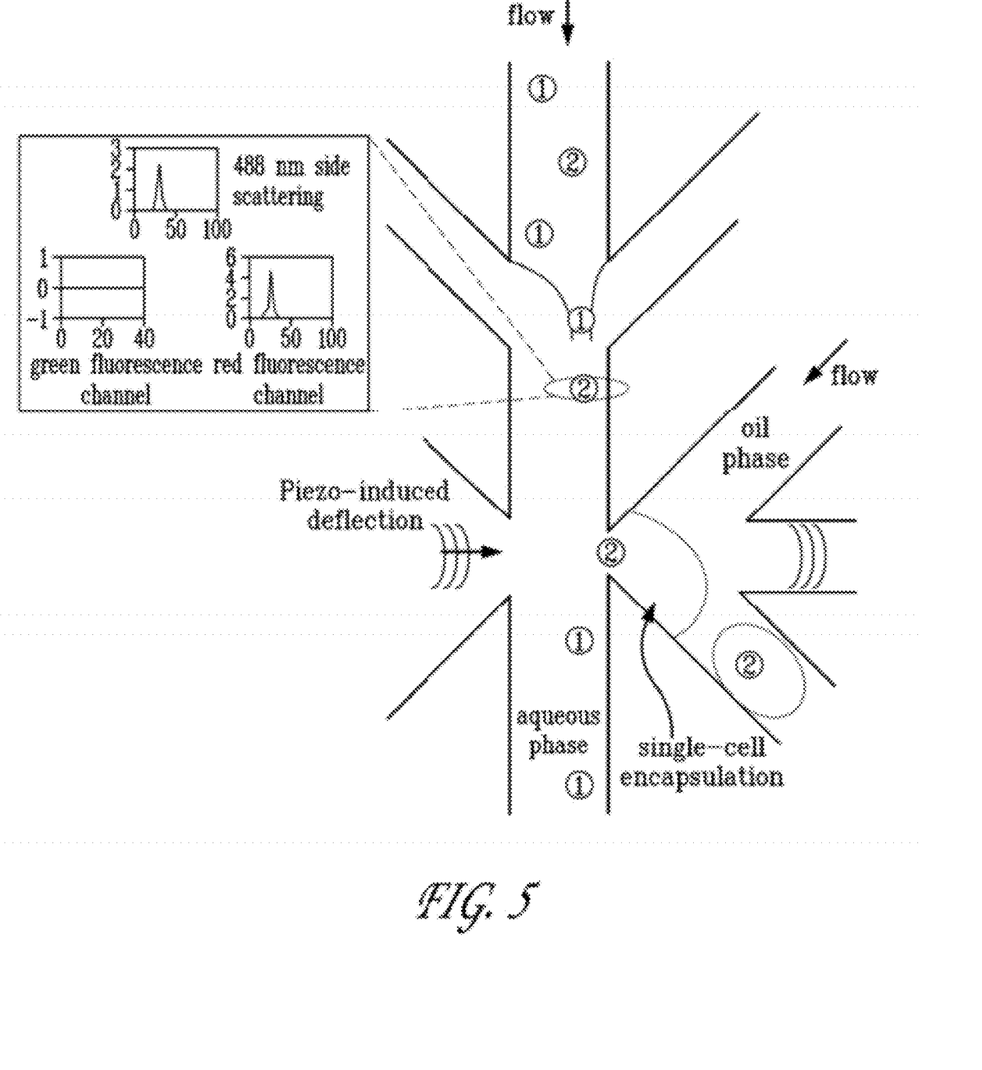
FIG. 5 schematically shows a particle of interest detected by forward scattering, which triggers displacement of a fluid packet by a piezo-actuated element. The inset shows the signals on the forward scattering and red fluorescence detectors. The fluid packet displaces the particle into a different microchannel containing a carrier fluid which is immiscible with the sample fluid, therefore encapsulating the particle into a discrete microdroplet.

In some embodiments, the methods and devices of the present invention may be used to encapsulate single particles into microdroplets or form microdroplets on demand or both. For example, instead of shifting individual particles of interest into a different laminar flow stream for downstream binning, a particle of interest may be deflected into a different microchannel containing a carrier fluid which is immiscible with the sample fluid as schematically shown in FIG. 5. For example, the sample fluid may be an aqueous fluid and the carrier fluid may be a non-aqueous fluid, such as oil or an organic solvent or vice versa. The immiscibility of the aqueous phase in a non-aqueous phase allows the formation of discrete, non-communicating picoliter-sized microdroplets. See Song & Ismagilov (2003) J. Am. Chem. Society 125: 14613-14619; He et al. (2005) Anal. Chem. 77:1539-1544; Moon et al. (2006) Lab on a Chip 6:1213-1219; Beer et al. (2007) Anal. Chem. 79:8471-8475; and Kim et al. (2007) Applied Physics Letts 91:113106, and Perroud et al. (2009) Lab On a Chip 9:507-515, which are herein incorporated by reference.

Prior art methods and devices for the encapsulation of particles in microdroplets show that the microdroplet occupancy (number of particles per microdroplet) follows a Poisson distribution. See Huebner et al. (2007) Chem. Comm. 12:1218-1220, which is herein incorporated by reference. For example, for every 1000 droplets having an averaged microdroplet occupancy of 0.065, we expect 937 empty microdroplets, 61 microdroplets with a single particle, and 2 microdroplets with two particles. To remove the heterogeneity in the microdroplet occupancy, an additional microdroplet sorting mechanism is required downstream of the encapsulation of particles in microdroplets. According to the present invention, the same fluid displacer, e.g. piezo-actuated element, simultaneously triggers both the formation of a microdroplet and the encapsulation of a particle into the same microdroplet. This approach has the advantage of creating microdroplets with a particle occupancy of 1, thus making the encapsulation of particles in microdroplets more efficient. Additionally, the fluid displacer, e.g. the piezo-actuated element, which triggers the formation of a microdroplet and the encapsulation of a particle into the microdroplet, is triggered by the signals of the sensors which are configured to sense a property of the particle to be encapsulated. Therefore, only selected particles of interest can be encapsulated into a microdroplet, making the encapsulation of particles of interest more efficient. This invention combines in a single-step three operations: (1) particles sorting, (2) microdroplet formation, and (3) particle encapsulation into a microdroplet.

As described herein, the present invention provides a system, including method and apparatus, for sorting particles, such as cells. The system may include two or more transport mechanisms for moving particles. A first of the transport mechanisms may be a nonselective mechanism configured to move a set of particles relatively continuously and non-selectively. The nonselective mechanism may operate, for example, by exerting a pressure on a fluid in which the set of particles is disposed and/or may exert a force on the set of particles in relation to the fluid. A second of the transport mechanisms may be a selective mechanism configured to selectively move a subset of the particles relative to other particles of the set, as the nonselective mechanism operates. Accordingly, the second transport mechanism may be pulse-activated at suitable times to selectively apply a force on particles of the subset. In accordance with the present invention, the selective mechanism is a closed-loop fluid circuit having a fluid displacer, such as a piezo-actuated element. Thus, the force is a pressure pulse, resulting from activation of the fluid displacer that is exerted on a fluid segment (fluid packet) in which the subset of particles is disposed. The force may be directed transversely to the direction in which the set of particles is transported by the nonselective transport mechanism, to move the subset of particles along a different path, thereby sorting the set of particles.

Closed-loop fluid circuits having fluid displacers, e.g. piezo-actuated elements, may be configured to operate concurrently, for parallel sorting of particles in a fluid sample. Alternatively, or in addition, the closed-loop fluid circuits having fluid displacers may be disposed in series for sequential sorting, for example, to provide progressive enrichment of a mixture for a particular type of particle. Enrichment, as used herein, may include any increase in the representation of one particle type relative to one or more other particle types of a mixture. For example, enrichment may increase the representation of a particular type of particle from a lower to a higher percentage of the particle total, and/or may substantially or completely separate the particular type of particle from one or more other types of particles.

A sample reservoir may be any vessel (or vessels) configured to receive the sample fluid and release portions of the sample fluid to a sorter(s). Release of the portions may be passive, such as through passage that is always in fluid communication with the sample reservoir, or active, such as with valve that operates to release portions selectively. The sample reservoir may be a well, a chamber, a channel, a syringe, or the like.

A conduit network may be any set of passages that provide fluid communication between the sample reservoir and the closed-loop fluid circuits having fluid displacers, e.g. piezo-actuated elements. The conduit network may include tubing, channels formed in or on a generally planar or three-dimensional channel structure, and/or a combination thereof, among others. The conduit network may include a set of parallel passages that extend from the sample reservoir to the closed-loop fluid circuits having fluid displacers, passages that increase in number or branch toward the closed-loop fluid circuits having fluid displacers, or a combination thereof. The conduit network may be defined by a manifold, as described below.

An output receptacle may be any vessel or compartment for receiving fluid and sorted particles from the closed-loop fluid circuits having fluid displacers, e.g. piezo-actuated elements. Exemplary output receptacles may include microplate wells, microfluidic compartments of a chip, test tubes, culture vessels, and the like. In some embodiments, each closed-loop fluid circuit having a fluid displacer may direct sorted particles to a separate output receptacle, for example, to perform post-sorting processing. The post-sorting processing may include cell culture, cell lysis, and/or molecular analysis (sensing) of cellular or particle constituents (such as analysis of a nucleic acid, protein, lipid, ion, carbohydrate, and the like). In an exemplary embodiment, post-sorting processing may include cell lysis followed by amplification of a nucleic acid.

The primary flow of the fluid sample resulting from a nonselective transport mechanism is through a primary microchannel which may be any structure that defines a passage along which particles may be transported. The passage may be any predefined path for particle/fluid travel. In addition, the passage may include walls and/or a particle guiding and/or fluid guiding surface characteristic, such as adjacent hydrophobic and hydrophilic surface regions. The primary microchannel may support the particles by supporting fluid in which the particles are disposed. Supported fluid, as used herein, is fluid that is in contact with a solid surface so that the fluid is restricted from falling. By contrast, unsupported fluid may include airborne fluid droplets. In some embodiments, the channel structure may be a substrate assembly including a substrate and a fluid barrier connected to the substrate, as described further below.

The primary microchannel may comprise more than flow paths. The primary microchannel may also comprise one or more intersections where the flow paths branch into secondary microchannels.

The systems and devices of the present invention may also contain one or more sensors which are configured to sense a property of each particle. The sensor may be an optical sensor that measures an optical (or electromagnetic) property of each particle, such as a luminescence, photoluminescence (for example, fluorescence or phosphorescence, chemiluminescence, or bioluminescence), scattering, absorbance, refraction, reflection, and/or polarization, among others. Alternatively, the sensor may be an electrical or magnetic sensor, configured to sense an electrical or magnetic property of the particles, respectively.

Sensors according to the present invention may be any suitable size, shape, location, and structure. In some embodiments, the sensor may be longer than the diameter of the particles, that is, long enough to sense a particle at a plurality of positions along a channel, for example, to measure the velocity of the particle. Accordingly, the sensor may be a single sensor or a plurality of sensor elements, which may be arrayed, for example, along a channel. The sensor also may have any suitable width including a width substantially similar to the width of a channel. The sensor may be formed on or below a surface of a channel, for example, one or more photodiodes formed on or in a substrate that defines a floor of the channel. The photodiodes may be configured to receive light selectively. Accordingly, they may be coated with a photos elective material, such as a filter layer that selectively permits the passage of particular wavelengths of light.

The nonselective transport mechanism may exert a similar force on different types of particles in a particle mixture so that they travel with a similar velocity. Alternatively, the nonselective transport mechanism may exert dissimilar forces so that different particles travel with different velocities. However, in either case, the nonselective transport mechanism moves the particles through a channel. The nonselective transport mechanism may be a continuous transport mechanism. A continuous transport mechanism, as used herein, may be any transport mechanism that moves a plurality of particles through the channel without substantial interruption.

The nonselective transport mechanism may operate by any suitable mechanism. For example, the nonselective transport mechanism may operate by exerting a force on a fluid in which the particles are disposed, to promote bulk fluid flow and concomitant bulk particle flow. Alternatively, this transport mechanism may exert a force on the particles relative to the fluid, to promote bulk particle flow through the fluid. The nonselective transport mechanisms may apply a positive or negative pressure to the fluid, generally upstream (toward the input mixture) or downstream (toward the receiver structures), respectively, so that there is a pressure drop along the channel. Exemplary nonselective transport mechanisms may include pressurized gas, a positive displacement pump (such as a syringe pump), a vacuum, and/or a peristaltic pump, among others. Other exemplary nonselective transport mechanisms may include electrodes arrayed to provide dielectrophoretic-based movement of the particles, for example, using traveling wave dielectrophoresis to propel a mixture of particles along the channel.

The fluid displacer, e.g. piezo-actuated element, in the closed-loop fluid circuit may be configured to act on individual particles or sets of particles of the mixture. In some embodiments, the particles in a fluid sample stream may be spaced sufficiently so that single particles may be displaced from the stream. Alternatively, the particles may not be spaced sufficiently, so that two or more particles may be displaced together. In either case, an enrichment of the mixture for a particular type(s) of particle, particularly a minor particle, may occur.

The fluid displacer, e.g. piezo-actuated element, may be pulse-activated, to provide a transient action on selected particles. Pulse-activated, as used herein, means activated by a transient signal pulse or a by a plurality of transient signal pulses. The transient signal pulses may be produced as needed to sort particles, generally separated by irregular time intervals, rather than being a steady signal or periodic signals occurring at regular intervals. Exemplary signal(s) may be an electrical signal (such as a current or voltage pulse) or an optical pulse that activates a phototransistor, among others.

The transient action on the selected particles and/or the transient signal pulses that activate the transport mechanism may be fast, that is, lasting for less than about one second. In some examples, the transient action may be a pressure pulse that lasts less than about ten milliseconds or less than about one millisecond, depending on parameters such as fluid viscosity, channel dimensions, channel geometry, and the like.

The selective transport mechanism may have any suitable maximum frequency of transport. The maximum frequency of transport is the maximum frequency of pressure pulses that can be produced per second and therefore the maximum number of particles that can be displaced by the selective transport mechanism per second. In some examples, the maximum frequency may be at least about 100 hertz or at least about one kilohertz.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of isolating a particle of interest from a plurality of particles in a fluid sample which comprises:
   identifying the particle of interest in a fluid stream flowing through a primary microchannel;
   inducing a fluid displacer in a closed-loop fluid circuit to give a secondary flow which causes a flow path and direction of the particle of interest that are different from that of the plurality of particles,
   wherein the closed-loop fluid circuit is a conduit having a fluid therein, said conduit links, in a closed-loop, a first side of the fluid displacer to a first side of the primary microchannel and a second side of the fluid displacer to a second side of the primary microchannel, such that the fluid displacer, when induced, simultaneously causes the first side of the fluid displacer to push the fluid in the conduit toward the first side of the primary microchannel and the second side of the fluid displacer to pull the fluid in the conduit from the second side of the primary microchannel toward the second side of the fluid displacer.

2. The method of claim 1, wherein the fluid displacer is bidirectional or unidirectional.

3. The method of claim 1, wherein the fluid displacer is a piezo-actuated element.

4. The method of claim 1, and further comprising focusing the plurality of particles to flow in single file through the primary microchannel.

5. The method of claim 1, and further comprising identifying a second particle of interest in the fluid stream and inducing a second fluid displacer in a second closed-loop fluid circuit to give a second secondary flow.

6. The method of claim 5, wherein the second fluid displacer may be the same or different from the fluid displacer, the second closed-loop fluid circuit may be the same or different closed-loop fluid displacer, the second secondary flow causes a second flow path and direction of the second particle of interest that may be the same or different from that of the particle of interest, or a combination thereof.

7. The method of claim 1, which comprises employing a plurality of fluid displacers to cause each particle of a plurality of particles to flow in a plurality of directions.

8. The method of claim 1, and further comprising encapsulating the particle of interest in a microdroplet.

9. The method of claim 1, wherein the particle of interest is encapsulated in a microdroplet by itself.

10. The method of claim 1, wherein actuation of the fluid displacer introduces a volume of fluid from the conduit into the primary microchannel and simultaneously removes a volume of fluid from the fluid stream from the primary microchannel, wherein the volume of the fluid from the conduit and the volume of fluid from the fluid stream are equal.

11. The method of claim 10, wherein the volume of fluid from the fluid stream that is removed from the primary microchannel is a fluid packet and the particle of interest is fully located within the fluid packet.

12. The method of claim 10, wherein fluid displacer is in direct fluidic communication with the fluid in the closed-loop fluid circuit.

13. The method of claim 1, wherein the closed-loop fluid circuit comprises an inline fluid displacer and two fluid conduits that link the sides of the fluid displacer to the respective sides of the primary flow path of the fluid sample.

14. The method of claim 1, wherein the closed-loop fluid circuit is at a transverse orientation to the primary flow path.

15. The method of claim 1, wherein the fluid in the closed-loop fluid circuit is compatible and miscible with the fluid in the primary microchannel.

16. A device which comprises:
   at least one primary microchannel; and
   at least one closed-loop fluid circuit which intersects the primary microchannel and comprises at least one fluid displacer, said closed-loop fluid circuit is configured to be a conduit that links, in a closed-loop, a first side of the fluid displacer to a first side of the primary microchannel and a second side of the fluid displacer to a second side of the primary microchannel, such that inducement of the fluid displacer simultaneously causes the first side of the fluid displacer to push a fluid in the conduit toward the first side of the primary microchannel and the second side of the fluid displacer to pull the fluid in the conduit from the second side of the primary microchannel toward the second side of the fluid displacer.

17. The device of claim 16, and further comprising at least one nonselective transport mechanism.

18. The device of claim 16, and further comprising a sample reservoir, a conduit network, an output receptacle, a sensor, a second microchannel which branches from the primary microchannel, or a combination thereof.

19. The device of claim 16, which comprises a plurality of closed-loop fluid circuits each having at least one fluid displacer which closed-loop fluid circuits are successively arranged along the length of the primary microchannel.

20. The device of claim 16, wherein the fluid displacer is bidirectional or unidirectional.

21. The device of claim 16, wherein the fluid displacer is a piezo-actuated element.

* * * * *